United States Patent
Neuba et al.

(10) Patent No.: US 10,034,822 B2
(45) Date of Patent: Jul. 31, 2018

(54) FASHIONABLE COPPER SHADES IN A NONIONIC BASE

(71) Applicant: Henkel AG & Co. KGaA, Duesseldorf (DE)

(72) Inventors: Constanze Neuba, Grevenbroich (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/379,136

(22) Filed: Dec. 14, 2016

(65) Prior Publication Data

US 2017/0172882 A1    Jun. 22, 2017

(30) Foreign Application Priority Data

Dec. 16, 2015 (DE) .......................... 10 2015 225 461

(51) Int. Cl.
*A61Q 5/10* (2006.01)
*A61K 8/49* (2006.01)
*A61K 8/22* (2006.01)
*A61K 8/73* (2006.01)
*B65D 81/32* (2006.01)

(52) U.S. Cl.
CPC ............... *A61K 8/494* (2013.01); *A61K 8/22* (2013.01); *A61K 8/4926* (2013.01); *A61K 8/73* (2013.01); *A61Q 5/10* (2013.01); *B65D 81/32* (2013.01); *A61K 2800/4324* (2013.01); *A61K 2800/88* (2013.01)

(58) Field of Classification Search
CPC ........ A61K 8/494; A61K 8/4926; A61K 8/73; A61K 2800/4324; A61K 2800/88; A61K 8/22; A61Q 5/10; B65D 81/32
See application file for complete search history.

(56) References Cited

U.S. PATENT DOCUMENTS

| 2002/0010970 A1* | 1/2002 | Cottard | A61K 8/342 8/405 |
| 2013/0205515 A1* | 8/2013 | Misu | A61K 8/411 8/401 |
| 2014/0298596 A1* | 10/2014 | Weser | A61K 8/411 8/405 |

FOREIGN PATENT DOCUMENTS

EP    1488783 A1 * 12/2004 ............... A61K 7/13

OTHER PUBLICATIONS

STIC Search Report dated Mar. 28, 2017.*
English transaltion (Sep. 6, 2017) of the EP Patent No. EP 1488783 A1.*

* cited by examiner

Primary Examiner — Eisa B Elhilo
(74) Attorney, Agent, or Firm — James J. Cummings

(57) ABSTRACT

An agent for oxidatively dyeing keratinous fibers, in particular human hair, includes —in a cosmetic carrier—
(A) 1-(2-hydroxyethyl)-4,5-diamino pyrazole and/or a physiologically acceptable salt thereof,
(B) 2,6-dihydroxy-3,4-dimethylpyridine,
(C) hydrogen peroxide, and
(D) one or more nonionic surfactants,
wherein the total content of all anionic surfactants (E) included in the agent is below 0.6 wt %, based on the total weight of the agent.
A second subject matter of the present invention is a corresponding multicomponent packaging unit (kit-of-parts).

20 Claims, No Drawings

FASHIONABLE COPPER SHADES IN A NONIONIC BASE

FIELD OF THE INVENTION

The present invention relates to an agent for oxidatively dyeing keratinous fibers, in particular human hair.

The present invention further relates to a multicomponent packaging unit (a "kit of parts") that includes at least two components that have been prepared separately from one another, for oxidatively dyeing keratinous fibers, in particular human hair.

BACKGROUND OF THE INVENTION

Changing the color of keratinous fibers, in particular hair, represents an important area of modern cosmetics. The appearance of the hair may thus be adapted to current fashion trends and to the person's individual preferences. Various options are known to those skilled in the art for changing the color of the hair. The hair color may be temporarily changed by using direct dyes. In the process, dyes which are already formed diffuse from the coloring agent into the hair fiber. Although coloration using direct dyes involves little damage to the hair, it is disadvantageous in that the colorings obtained with direct dyes are not very durable and wash out quickly.

If the consumer desires a long-lasting color result or a shade that is lighter than his/her original hair color, oxidative color-changing agents are customarily used. For permanent, intense colorations having appropriate fastness properties, so-called oxidation dyes are used. Such coloring agents customarily include oxidation dye precursors, so-called developer components and coupler components, which form the actual dyes with one another under the influence of oxidizing agents. Oxidation dyes are characterized by long-lasting color results.

Extensive prior art already exists with regard to oxidative coloring agents. Considerable testing has been conducted, in particular for optimizing the color intensity and fastness properties of fashionable shades.

However, despite the large number of optimization tests already carried out, there is still a need for improvement of the color intensity of oxidatively dyed keratin fibers, in particular when they are colored in a fashionable reddish shade. In particular, the color intensity and shade outcome of copper shades cannot yet be considered to be optimal.

The wash fastness of a color shade is understood to mean the change in color of the hair strands colored with this shade under the influence of multiple hair washings. This change in color may involve a shift of the color toward another hue, or also lightening of the coloring. Both changes in color are equally undesirable to the user. Color shades with good wash fastness experience little or no change in color, even after repeated hair washings. The hair washing may take place using a shampoo, a conditioning shampoo, or a conditioner.

An improved shade outcome and enhanced brilliance are understood, within the framework of the present invention, to mean that the copper shade that can be achieved with the agents impart overall a more fashionable—i.e., more intense and reddish—impression without a brown tint. The color richness can be quantified in colorimetric measurements, by determining the chroma value (C).

Keratinous fibers can be dyed in copper tones when a specific combination of (A) the developer 1-(2-hydroxyethyl)-4,5-diamino pyrazole and (B) the coupler 2,6-dihydroxy-3,4-dimethylpyridine is used in the coloring agents. Corresponding agents are known, for example, from EP 1488783 A1. In these formulations known from the prior art, however, there is always at least one anionic surfactant present in the ready-to-use oxidative coloring agent.

Desirable features and characteristics of the present invention will become apparent from the subsequent detailed description of the invention and the appended claims, taken in conjunction with this background of the invention.

BRIEF SUMMARY OF THE INVENTION

An agent for oxidatively dyeing keratinous fibers, in particular human hair, includes—in a cosmetic carrier—(A) 1-(2-hydroxyethyl)-4,5-diamino pyrazole and/or a physiologically acceptable salt thereof; (B) 2,6-dihydroxy-3,4-dimethylpyridine; and (C) hydrogen peroxide; and (D) one or more nonionic surfactants, wherein the total content of all anionic surfactants (E) included in the agent is below 0.6 wt %, based on the total weight of the agent.

A multicomponent packaging unit (kit-of-parts) for oxidatively dyeing keratinous fibers, includes at least two components (K1) and (K2) prepared separately from one another, wherein the first component (K1) includes, in a cosmetic carrier, (A) 1-(2-hydroxyethyl)-4,5-diamino pyrazole and/or a physiologically acceptable salt thereof; (B) 2,6-dihydroxy-3,4-dimethylpyridine; and (D') one or more nonionic surfactants, the second component (K2) includes, in a cosmetic carrier, (C) hydrogen peroxide; and (D") one or more nonionic surfactants, the total content of all of the anionic surfactants (E) included in the component (K1)—based on the total weight of the component (K1)—is below 0.6 wt %, and the total content of all of the anionic surfactants (E) included in the component (K2)—based on the total weight of the component (K2)—is below 0.6 wt %.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention addresses the problem of providing oxidative coloring agents for achieving brilliant copper shades with improved color intensity, optimized shade outcome, and enhanced brilliance and color richness. In addition, the shades that can be achieved with these agents should possess improved fastness properties, in particular an improved wash fastness.

In the course of the work conducted for the present invention, it has now been found that the presence of the anionic surfactant(s) exerts a significant influence on the shade outcome.

Thus, though an intensive color result can still be achieved from an anionic cream base with the use of (A) 1-(2-hydroxyethyl)-4,5-diamino pyrazole and (B) 2,6-dihydroxy-3,4-dimethylpyridine, the shade outcome is then shifted toward a more natural, brown-tinted copper tone. This brownish shade outcome may be desirable for the development of natural color shades. If, however, purely fashionable and brilliant copper shades are to be developed, then this is not possible with the formulations known from the prior art.

It has surprisingly been found that it is possible to achieve especially fashionable and brilliant color results with the combination of (A) 1-(2-hydroxyethyl)-4,5-diamino pyrazole and (B) 2,6-dihydroxy-3,4-dimethylpyridine, if these oxidation dye precursors are incorporated into a nonionic cream formulation in which anionic surfactants are included in the lowest total concentrations possible.

A first subject matter of the present invention is an agent for oxidatively dyeing keratinous fibers, in particular human hair, including—in a cosmetic carrier—

(A) 1-(2-hydroxyethyl)-4,5-diamino pyrazole and/or a physiologically acceptable salt thereof, (B) 2,6-dihydroxy-3,4-dimethylpyridine, (C) hydrogen peroxide, and (D) one or more nonionic surfactants, wherein the total content of all anionic surfactants (E) included in the agent is below 0.6 wt %, based on the total weight of the agent.

Keratinous fibers, keratin-containing fibers, or keratin fibers are understood to mean fur, wool, feathers, and in particular human hair. Although the agents according to the present invention are primarily suited for dyeing keratin fibers, use in other fields is also possible in principle.

The term "agent for oxidatively dyeing" as used according to the present invention is understood to mean oxidative coloring agents that include oxidation dye precursors of the developer type and coupler type. The dyeing is carried out through the presence of an oxidizing agent, which involves hydrogen peroxide (C). Depending on the quantity of oxidizing agent employed, the keratin fibers are simultaneously lightened to a greater or less extent during coloring, since the oxidizing agent not only initiates the dye-forming process of the developers and couplers, but also oxidatively destroys the hair's own pigments (melanins).

The agents include the oxidation dye precursors (A) and (B) as well as the oxidizing agent (C) and the nonionic surfactant(s) (D) in a cosmetic carrier, preferably in a suitable aqueous, alcoholic, or aqueous-alcoholic carrier. For purposes of the oxidative change in color, such carriers may be, for example, creams, emulsions, gels, or also foaming solutions such as shampoos, foam aerosols, foam formulations, or other preparations that are suitable for application to the hair. Agents for oxidatively dyeing keratinous fibers are particularly preferably creams or emulsions.

The content of the oxidation dye precursor of the developer type (A) and the oxidation dye precursor of the coupler type (B) is characterizing for the agents according to the present invention.

Within the meaning of the present invention, a developer is understood to mean an oxidation dye precursor of the developer type. Within the meaning of the present invention, a coupler is understood to mean an oxidation dye precursor of the coupler type.

As the first oxidation dye precursor of developer type (A), the agents according to the present invention include 4,5-diamino-1-(2-hydroxyethyl)-1H-pyrazole and/or one of the physiologically acceptable salts thereof.

4,5-diamino-1-(2-hydroxyethyl)-1H-pyrazole is the compound of the formula (i).

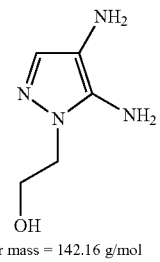

(i)

molar mass = 142.16 g/mol

Preferred physiologically acceptable salts of 4,5-diamino-1-(2-hydroxyethyl)-1H-pyrazole are in particular the hydrochlorides (monohydrochloride×HCl, or dihydrochloride×2 HCl), the sulfate (×H$_2$SO$_4$), and the hydrobromides (monohydrobromide×HBr, or dihydrobromide×2 HBr) of the compound. 4,5-Diamino-1-(2-hydroxyethyl)-1H-pyrazole sulfate (formula (ii)) is very particularly preferred.

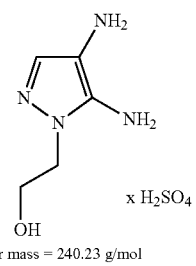

(ii)

molar mass = 240.23 g/mol 1-(2-Hydroxyethyl)-4,5-diamino pyrazole (A) is very particularly preferably used in the form of the sulfate salt, in an amount of 0.025 to 2.5 wt %, preferably 0.05 to 1.0 wt %, further preferably 0.1 to 0.7 wt %, and especially preferably 0.1 to 0.5 wt %. The amount is given here on the basis of the weight of 1-(2-Hydroxyethyl)-4,5-diamino pyrazole sulfate that is used in relation to the total weight of the agent.

In a particularly preferred embodiment, an agent according to the present invention is therefore characterized by including—based on the total weight of the agent—(A) 0.025 to 2.5 wt %, preferably 0.05 to 1.0 wt %, further preferably 0.1 to 0.7 wt %, and especially preferably 0.1 to 0.5 wt % 1-(2-hydroxyethyl)-4,5-diamino pyrazole sulfate.

As a second essential component (B), the agents according to the present invention include 2,6-dihydroxy-3,4-dimethylpyridine as an oxidation dye precursor of the coupler type. 2,6-Dihydroxy-3,4-dimethylpyridine is a heterocyclic dihydroxy compound of the formula (iii).

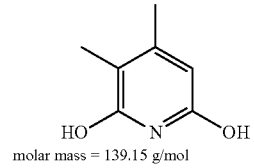

(iii)

molar mass = 139.15 g/mol 2,6-Dihydroxy-3,4-dimethylpyridine (B) is preferably used in the form of the free compound thereof.

2,6-Dihydroxy-3,4-dimethylpyridine (B) is especially preferably used in an amount of 0.025 to 1.5 wt %, preferably 0.05 to 1.0 wt %, further preferably 0.1 to 0.5 wt %, and especially preferably 0.1 to 0.3 wt %. The amount is given here on the basis of the weight of 2,6-dihydroxy-3,4-dimethylpyridine (B) included in the agent that is used in relation to the total weight of the agent.

In a particularly preferred embodiment, an agent according to the present invention is therefore characterized by including—based on the total weight of the agent—(B) 0.025 to 1.5 wt %, preferably 0.05 to 1.0 wt %, further preferably 0.1 to 0.5 wt %, and especially preferably 0.1 to 0.3 wt % 2,6-dihydroxy-3,4-dimethylpyridine.

As a third essential component, the agent for oxidatively dyeing keratinous fibers according to the present invention includes hydrogen peroxide (C).

Once the oxidation dye precursors (A and B) come into contact with the oxidizing agent (C), the coupling process initiated by the oxidizing agent (C) starts, and the dye formation begins. The agent according to the present invention including the ingredients (A), (B), and (C) is thus the ready-to-use oxidative coloring agent. All amounts related to the total weight of the agent according to the present invention are therefore given on the basis of the total weight of the ready-to-use agent.

Preferably, the amount of oxidizing agent in the agent according to the present invention is 0.5 to 12 wt %, preferably 2 to 10 wt %, particularly preferably 3 to 6 wt % (calculated as 100% $H_2O_2$), based in each case on the total weight of the agent according to the present invention.

The amount of oxidizing agent is to be selected by a person skilled in the art on the basis of the desired lightening power. If the formation of a very dark, fashionable copper shade is desired, a person skilled in the art would accordingly reduce the amount of hydrogen peroxide used. If, however, a brilliant fashionable shade for dark hair is intended, the hair must also be lightened to a significant extent at the same time. In this case, a higher amount of hydrogen peroxide used is accordingly selected.

The selection of the suitable base into which the previously-described oxidation dyes are incorporated and from which they are dyed plays a very important role in dyeing the keratin fibers with the highest possible brilliance. It has been found that the chroma of the dyes is then especially high when the base formulation for the dyes includes at least one nonionic surfactant (D), and when the base formulation is moreover as free as possible of surfactants having an anionic charge. For this reason, it is also an essential feature that the total content of all anionic surfactants (E) included in the agent according to the present invention is below 0.6 wt %, based on the total weight of the agent.

A "surfactant" in the sense of the present invention is understood to be a compound having one hydrophobic moiety and one hydrophilic moiety. The hydrophobic residue is, according to the present invention, a preferably linear hydrocarbon chain (i.e., an alkyl chain) having at least 8 carbon atoms. A surfactant is a surface-active substance that is capable of reducing the interfacial tension.

A nonionic surfactant (D) is a surfactant that bears no charge or charges. In other words, a nonionic surfactant includes no dissociable functional groups, and is therefore unable to separate into ions in water. Nonionic surfactants, too, are composed of a non-polar part, preferably a hydrocarbon chain (alkyl chain) having at least eight carbon atoms, and a polar part. As a polar part, the nonionic surfactant may include, for example, a polyethylene glycol unit or a monosaccharide or polysaccharide unit.

Fatty alcohols ($C_8$-$C_{30}$ alkanols) having a fat chain and only one hydroxy group are very poorly soluble in water and do not have a sufficiently polar moiety. Therefore, fatty alcohols in the sense of the present invention are considered to be fatty components and explicitly not to be nonionic surfactants.

The monoesters and diesters of fatty alcohols (i.e., $C_8$-$C_{30}$ alkanols) and ethylene glycol are considered to be fatty substances and explicitly not to be nonionic surfactants.

The monoesters, diesters, and triesters of fatty alcohols (i.e., $C_8$-$C_{30}$ alkanols) and glycerol are considered to be fatty substances and explicitly not to be nonionic surfactants.

As further components (D) that are essential to the present invention, the agents according to the present invention include at least one nonionic surfactant. The presence of at least one nonionic surfactant (D) is a prerequisite for dyeing the keratin fibers in especially brilliant and fashionable shades.

Suitable nonionic surfactants (D) include as a hydrophilic group, for example, a polyol group, a polyalkylene glycol ether group or a combination of a polyol and polyglycol ether group. Such compounds include, for example addition products of 5 to 50 mol of ethylene oxide and/or 5 to 50 mol of propylene oxide with linear and branched fatty alcohols having 8 to 30 C atoms—for example, lauryl, myristyl, cetyl, or even stearyl, isostearyl, and oleyl alcohols—with fatty acids having 8 to 30 C atoms, and with alkyl phenols having 8 to 15 C atoms in the alkyl group;

addition products—end-capped with a methyl or $C_2$-$C_6$ alkyl residue—of 5 to 50 mol of ethylene oxide and/or 5 to 50 mol of propylene oxide with linear and branched fatty alcohols having 8 to 30 C atoms, with fatty acids having 8 to 30 C atoms and with alkylphenols having 8 to 15 C atoms in the alkyl group, such as those available under the commercial names Dehydrol® LS, Dehydrol® LT (Cognis);

polyglycerol esters and alkoxylated polyglycerol esters, such as for example poly(3)glycerol diisostearate (commercial product: Lameform® TGI (Henkel)) and poly(2)glycerol polyhydroxystearate (commercial product: Dehymuls® PGPH (Henkel)).

polyol fatty acid esters, such as the commercial product Hydagen® HSP (Cognis) or Sovermol-types (Cognis), more highly alkoxylated, preferably propoxylated and in particular ethoxylated mono-, di- and triglycerides, such as glycerol monolaurate+20 ethylene oxide and glycerol monostearate+20 ethylene oxide, amine oxides;

hydroxy mixed ethers, sorbitan fatty acid esters and addition products of ethylene oxide to sorbitan fatty acid esters, such as e.g. polysorbates and sorbitol monolaurate+20 mol ethylene oxide (EO), sugar fatty acid esters and addition products of ethylene oxide to sugar fatty acid esters, addition products of ethylene oxide to fatty acid alkanolamides and fatty amines, fatty acid-N-alkyl glucamides, alkylphenols and alkylphenol alkoxylates having 6 to 21, in particular 6 to 15, carbon atoms in the alkyl chain and 1 to 30 ethylene oxide and/or propylene oxide units. Preferred representatives of this class include nonylphenol+9 EO and octylphenol+8 EO;

alkyl polyglycosides corresponding to the general formula RO—$(Z)_x$ wherein R denotes an alkyl, Z denotes a sugar, and x denotes the number of sugar units. Alkyl polyglycosides usable according to the present invention may include only one specific alkyl residue R. However, these compounds are normally prepared from natural fats and oils or mineral oils. In this case, the alkyl groups R are present as mixtures corresponding to the starting compounds or to the particular working-up of those compounds.

To produce especially brilliant color shades, however, very specific nonionic surfactants (D) have proven to be especially favorably suitable. In this context, in particular, ethoxylated fatty alcohols and $C_8$-$C_{22}$ alkyl mono- and oligoglycosides have turned out to be especially advantageous.

In a particularly preferred embodiment, an agent according to the present invention is therefore characterized by including, as a nonionic surfactant (D1), one or more ethoxylated fatty alcohols of the formula (I),

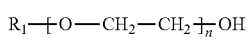

where
$R^1$ denotes a saturated or unsaturated unbranched or branched $C_8$-$C_{30}$ alkyl group, preferably a saturated unbranched $C_{16}$ or $C_{18}$ alkyl group, and
n denotes an integer from 10 to 120, preferably an integer from 10 to 80, further preferably an integer from 10 to 50, and especially preferably an integer from 10 to 30.

In another particularly preferred embodiment, an agent according to the present invention is characterized by including, as a nonionic surfactant (D2), one or more alkyl monoglucosides or polyglucosides of the formula (II),

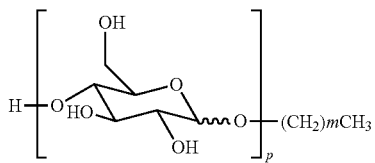

where
m denotes an integer 7 to 21, preferably 9 to 19, further preferably 9 to 17, and especially preferably 11 to 15, and
p denotes an integer 1 to 4, preferably 1 to 3, and especially preferably 1 to 2.

The nonionic surfactant(s) (D) is/are preferably used in an amount within certain ranges in order to achieve a particularly fashionable shade outcome. It has turned out to be especially advantageous when the (ready-to-use) agent according to the present invention includes the nonionic surfactant(s)—based on the total weight of the agent—in a total content of 0.5 to 5.0 wt %, preferably 0.7 to 4.0 wt %, further preferably 1.0 to 3.5 wt %, and especially preferably 1.2 to 2.5 wt %.

In another especially preferred embodiment, an agent according to the present invention is therefore characterized in that the total content of all nonionic surfactants (D) included in the agent—based on the total weight of the agent—is 0.3 to 5.0 wt %, preferably 0.4 to 4.0 wt %, further preferably 1.0 to 3.5 wt %, and especially preferably 1.2 to 2.5 wt %.

As previously stated, the selection of the suitable base into which the oxidation dye precursors (A) and (B) are incorporated is a major decisive factor for the generation of dyes having the highest possible brilliance. The use of a nonionic base is very significantly advantageous for producing brilliant dyes. A series of experiments have shown that the presence of anionic surfactants (E) shifts the shade outcome in the direction of brown tones. Here, the higher the total content of anionic surfactants (E) in the ready-to-use coloring agent, the more pronounced the brown shift.

As a result, it is also an essential feature that the total content of all anionic surfactants (E) included in the (ready-to-use) agent according to the present invention is below 0.6 wt %, based on the total weight of the agent.

An anionic surfactant in the sense of the present invention is a surfactant that bears an anionic charge. Anionic surfactants, by definition, bear no cationic charge, i.e., a zwitterionic surfactant does not fall under the group of anionic surfactants.

In other words, an anionic surfactant is characterized by having a non-polar part, preferably a hydrocarbon chain (alkyl chain) having at least eight carbon atoms, and a polar part. The polar moiety is a negatively-charged functional group that carries at least one negative charge. The negatively-charged functional group is, for example, —COO⁻ (carboxylate), —SO₃⁻ (sulfonate), —OSO₃⁻ (sulfuric acid half-ester), —OP(O)O₂²⁻ (phosphate, doubly deprotonated) or —OP(O)(OH)O⁻ (phosphate, singly deprotonated), or —P(O)O₂²⁻ (phosphonate, doubly deprotonated), or P(O)(OH)O— (phosphonate, singly deprotonated).

In addition to the anionic group, the anionic surfactant may also include glycol, polyglycol ether, ester, ether, and amide groups, as well as hydroxy groups. Examples of anionic surfactants—each example being in the form of the corresponding sodium, potassium, ammonium, or mono-, di-, or trialkanolammonium salt thereof having 2 to 4 C atoms in the alkanol group—are:

linear and branched fatty acids having 8 to 30 C atoms (soaps);
ether carboxylic acids of the formula RO(CH₂CH₂O)ₓCH₂COOH, in which R is a linear alkyl group having 8 to 30 C atoms and x=0 or 1 to 16;
acyl sarcosides having 8 to 24 C atoms in the acyl group;
acyl taurides having 8 to 24 C atoms in the acyl group;
acyl isethionates having 8 to 24 C atoms in the acyl group;
sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups;
linear alkane sulfonates having 8 to 24 C atoms;
linear α-olefin sulfonates having 8 to 24 C atoms;
sulfonates of unsaturated fatty acids having 8 to 24 C atoms and 1 to 6 double bonds,
α-sulfo fatty acid methyl esters of fatty acids having 8 to 30 C atoms;
alkyl sulfates and alkyl ether sulfates of the formula RO(CH₂CH₂O)ₓSO₃H, in which R is a preferably linear alkyl group having 8 to 30 C atoms and x=0 or 1 to 12;
mixtures of surface-active hydroxy sulfonates,
sulfated hydroxyalkyl polyethylene and/or hydroxyalkylene propylene glycol ethers,
esters of tartaric acid and citric acid with alcohols, which represent addition products of about 2-15 molecules ethylene oxide and/or propylene oxide to fatty alcohols having 8 to 22 C atoms,
alkyl and/or alkenyl ether phosphates of the formula

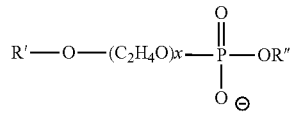

in which R' denotes an aliphatic, optionally unsaturated hydrocarbon residue having eight to 30 carbon atoms, R" denotes hydrogen, a residue $(CH_2CH_2O)_yR'$, and x and y denote a number 1 to 10 independently of one another, sulfated fatty acid alkyl glycol esters of the formula $RC(O)O(alkO)_nSO_3$—, in which R denotes a linear or branched aliphatic saturated and/or unsaturated alkyl residue having eight to 22 C atoms, alk denotes $CH_2CH_2$, $CHCH_3CH_2$, and/or $CH_2CHCH_3$, and n denotes a number 0.5 to 5, monoglyceride sulfates and monoglyceride ether sulfates.

Of all the surfactants, anionic surfactants have the best cleaning effect. Therefore, if a significant cleaning is intended to be achieved in addition to dyeing, it may be necessary to add anionic surfactants in a low total amount to the agent according to the present invention. The lower total content of all aforementioned anionic surfactants (E) in the agent according to the present invention, the more brilliant and fashionable the color result. Therefore, it is especially preferable when the total content of the anionic surfactants in the agent according to the present invention is below 0.5 wt %, preferably below 0.4 wt %, further preferably below 0.3 wt %, and especially preferably below 0.1 wt %. Here, all quantities given in wt % are based on the total weight of all anionic surfactants (E) included in the agent, which is set in relation to the total weight of the agent.

In another especially preferred embodiment, an agent according to the present invention is therefore characterized in that the total content of all anionic surfactants (E) included in the agent—based on the total weight of the agent—is below 0.5 wt %, preferably below 0.4 wt %, further preferably below 0.3 wt %, and especially preferably below 0.1 wt %.

In this context, it has been found that the presence of the
(E1) sodium, potassium, and ammonium salts of fatty acids R'COOH and/or
(E2) sodium, potassium, and ammonium salts of alkyl sulfates $R'OSO_3H$ and/or
(E3) sodium, potassium, and ammonium salts of alkyl ether sulfates $R'O(CH_2CH_2O)_xSO_3H$ and/or
(E4) sodium, potassium, and ammonium salts of ether carboxylic acids $R'O(CH_2CH_2O)_xCH_2COOH$,
wherein R' in each case denotes a $C_8$-$C_{30}$ alkyl group and x denotes an integer from 1 to 30, provokes an especially intense brown shift.

In the formulae above, each residue R' in one formula (E1) to (E4) may be selected independently of the other residues R' in the other formulae (E1) to (E4).

In much the same manner, in the formulae above, each residue x in one formula (E3) to (E4) may be selected independently of the other residue x in the other formulae (E3) to (E4).

In another especially preferred embodiment, therefore, the total amount of anionic surfactants (E1) to (E4) in the agent according to the present invention is selected so as to be especially low. Preferably, therefore, the total amount of the anionic surfactants (E1) to (E4)—based on the total weight of the agent—is preferably below 0.3 wt %, preferably below 0.2 wt %, and especially preferably below 0.1 wt %.

In an especially preferred embodiment, the agents according to the present invention are free of each of the anionic surfactants (E1) to (E4).

In another especially preferred embodiment, an agent according to the present invention is therefore characterized in that the total content of all of the anionic surfactants included in the agent from the group of
(E1) sodium, potassium, and ammonium salts of fatty acids and
(E2) sodium, potassium, and ammonium salts of alkyl sulfates and
(E3) sodium, potassium, and ammonium salts of alkyl ether sulfates and
(E4) sodium, potassium, and ammonium salts of ether carboxylic acids
based on the total weight of the agent—is below 0.3 wt %, preferably below 0.2 wt %, and especially preferably below 0.1 wt %.

In another especially preferred embodiment, an agent according to the present invention is, in other words, characterized in that the total content of all of the anionic surfactants included in the agent from the group of
(E1) sodium, potassium, and ammonium salts of fatty acids R'COOH and
(E2) sodium, potassium, and ammonium salts of alkyl sulfates $R'OSO_3H$ and
(E3) sodium, potassium, and ammonium salts of alkyl ether sulfates $R'O(CH_2CH_2O)_xSO_3H$ and
(E4) sodium, potassium, and ammonium salts of ether carboxylic acids $R'O(CH_2CH_2O)_xCH_2COOH$,
wherein R' in each case denotes a $C_8$-$C_{30}$ alkyl group and x denotes an integer from 1 to 30,
based on the total weight of the agent—is below 0.3 wt %, preferably below 0.2 wt %, and especially preferably below 0.1 wt %.

It has furthermore been shown that a shifting of shade of the color result from (A) and (B) occurring in the brown direction is provoked not only by the negatively-charged anionic surfactants, but also—though in not such a pronounced manner—by the zwitterionic surfactants.

It has been inferred, without being limited to this theory, that the shift in color of the color result to brown is provoked by the negative charges that are present both in anionic surfactants and in zwitterionic surfactants. Cationic surfactants cause no such color shift, according to what is known thus far.

A zwitterionic surfactant in the sense of the present invention is understood to be a surface-active compound that possesses both a negatively-charged functional group and a positively-charged functional group. As with any surfactant, the zwitterionic surfactants are also composed of a polar part and a non-polar part. Serving as the non-polar part is a hydrocarbon chain (i.e., alkyl chain) having at least eight carbon atoms, while the polar part is usually a carboxylate group (R—COO$^-$), a sulfonate group, or a sulfate group together with a quaternary ammonium group ($R_4N^+$).

Particularly well-known zwitterionic surfactants are the so-called betaines, such as the N-alkyl-N,N-dimethylammonium glycinates, for example cocoalkyl dimethylammonium glycinate; the N-acylaminopropyl-N,N-dimethylammonium glycinates, for example cocoacylaminopropyl dimethylammonium glycinate; and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A corresponding zwitterionic surfactant is the fatty acid amide derivative known by the INCI designation cocamidopropyl betaine.

In another especially preferred embodiment, an agent according to the present invention is characterized in that the total content of all zwitterionic surfactants (F) included in the agent—based on the total weight of the agent—is below 0.5 wt %, preferably below 0.4 wt %, further preferably below 0.3 wt %, and especially preferably below 0.1 wt %.

The total content of all of the zwitterionic surfactants is understood to be the total weight of all of the zwitterionic surfactants included in the agent, which is set in relation to the total weight of the agent.

To achieve finer shading of the desired copper shade, the agents according to the present invention may also additionally include yet another one or more further oxidation dyes of the developer type. In particular, if at least one compound from the group of p-phenylenediamine, toluene-2,5-diamine, 2-(2,5-diaminophenyl)ethanol, and/or the physiologically acceptable salts of these compounds is also added to the combination of (A) and (B), favorable results could be obtained.

In another especially preferred embodiment, an agent according to the present invention is characterized by additionally including one or more compounds from the group of p-phenylenediamine, toluene-2,5-diamine, 2-(2,5-diaminophenyl)ethanol, and/or the physiologically acceptable salts of these compounds.

p-Phenylenediamine is a compound of the following formula:

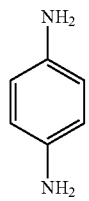

molar mass = 108.14 g/mol.

Toluene-2,5-diamine (alternative names: p-toluylenediamine, 2-methyl-p-phenylenediamine) is a compound of the following formula:

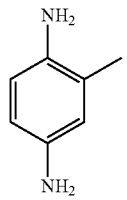
(E2)

molar mass = 122.17 g/mol.

2-(2,5-Diaminophenyl)ethanol is a compound of the following formula:

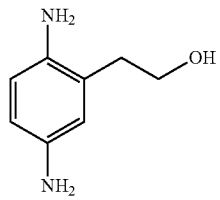

molar mass = 152.20 g/mol.

Preferred physiologically acceptable salts of p-phenylenediamine are in particular the hydrochlorides (monohydrochloride×HCl, or dihydrochloride×2 HCl), the sulfate (×H$_2$SO$_4$), and the hydrobromides (monohydrobromide×HBr, or dihydrobromide×2 HBr) of the compound.

Preferred physiologically acceptable salts of toluene-2,5-diamine are in particular the hydrochlorides (monohydrochloride×HCl, or dihydrochloride×2,5 HCl), the sulfate (×H$_2$SO$_2$), and the hydrobromides (monohydrobromide×HBr, or dihydrobromide×4 HBr) of the compound. Toluene-2,5-diamine sulfate is especially preferred.

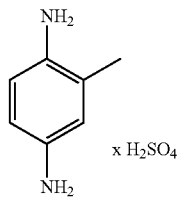

molar mass = 220.392 g/mol (toluene-2,5-diamine sulfate)

Preferred physiologically acceptable salts of 2-(2,5-diaminophenyl)ethanol are in particular the hydrochlorides (monohydrochloride×HCl, or dihydrochloride×2 HCl), the sulfate (×H$_2$SO$_4$), and the hydrobromides (monohydrobromide×HBr, or dihydrobromide×2 HBr) of the compound. 2-(2,5-Diaminophenyl)ethanol is especially preferred.

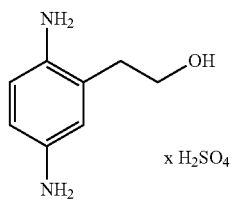

molar mass = 250.27 g/mol (2-(2,5-Diaminophenyl)ethanol sulfate)

The experiments leading to the present invention have shown that adding one or more developers from the group to the combination of 1-(2-hydroxyethyl)-4,5-diamino pyrazole (A) and 2,6-dihydroxy-3,4-dimethylpyridine (B) makes it possible to develop brilliant copper shades, which are additionally distinguished by a significant improvement in the wash fastness and the gray coverage.

Toluene-2,5-diamine and/or one of the physiologically acceptable salts thereof have proven especially suitable in this context.

In a particularly preferred embodiment, an agent according to the present invention is therefore characterized by including toluene-2,5-diamine and/or one of the physiologically acceptable salts thereof.

In other words, an agent according to the present invention is, in a particularly preferred embodiment, characterized by additionally including toluene-2,5-diamine, toluene-2,5-diamine monohydrochloride, toluene-2,5-diamine dihydrochloride, toluene-2,5-diamine monohydrobromide, toluene-2,5-diamine dihydrobromide, and/or toluene-2,5-diamine sulfate.

In an especially preferred embodiment, an agent according to the present invention is characterized by including toluene-2,5-diamine sulfate.

Adding the developer 2-(2,5-diaminophenyl)ethanol and/or one of the physiologically acceptable salts thereof to the combination of (A) and (B) also makes it possible to significantly improve the wash fastness and gray coverage of the copper shade.

In another particularly preferred embodiment, an agent according to the present invention is therefore characterized by including 2-(2,5-diaminophenyl)ethanol and/or one of the physiologically acceptable salts thereof.

In other words, an agent according to the present invention is, in an especially preferred embodiment, characterized by including 2-(2,5-diaminophenyl)ethanol, 2-(2,5-diaminophenyl)ethanol monohydrochloride, 2-(2,5-diaminophenyl)ethanol dihydrochloride, 2-(2,5-diaminophenyl)ethanol monohydrobromide, 2-(2,5-diaminophenyl)ethanol dihydrobromide, and/or 2-(2,5-diaminophenyl)ethanol sulfate.

In an especially preferred embodiment, an agent according to the present invention is therefore characterized by including 2-(2,5-diaminophenyl)ethanol sulfate.

Especially preferred is an agent for oxidatively dyeing keratinous fibers that includes, in a cosmetic carrier, based on the total weight of the agent,
(A) 0.025 to 2.5 wt % 1-(2-hydroxyethyl)-4,5-diamino pyrazole sulfate, and
(B) 0.025 to 1.5 wt % 2,6-dihydroxy-3,4-dimethylpyridine, and
additionally 0.007 to 1.5 wt % toluene-2,5-diamine sulfate.

Especially preferred is an agent for oxidatively dyeing keratinous fibers that includes, in a cosmetic carrier, based on the total weight of the agent,
(A) 0.05 to 1.0 wt % 1-(2-hydroxyethyl)-4,5-diamino pyrazole sulfate, and
(B) 0.05 to 1.0 wt % 2,6-dihydroxy-3,4-dimethylpyridine, and
additionally 0.007 to 0.7 wt % toluene-2,5-diamine sulfate.

Especially preferred is an agent for oxidatively dyeing keratinous fibers that includes, in a cosmetic carrier, based on the total weight of the agent,
(A) 0.1 to 0.7 wt % 1-(2-hydroxyethyl)-4,5-diamino pyrazole sulfate,
(B) 0.1 to 0.5 wt % 2,6-dihydroxy-3,4-dimethylpyridine, and
additionally 0.007 to 0.15 wt % toluene-2,5-diamine sulfate.

Especially preferred is an agent for oxidatively dyeing keratinous fibers that includes, in a cosmetic carrier, based on the total weight of the agent,
(A) 0.1 to 0.5 wt % 1-(2-hydroxyethyl)-4,5-diamino pyrazole sulfate,
(B) 0.1 to 0.3 wt % 2,6-dihydroxy-3,4-dimethylpyridine, and
additionally 0.07 to 0.1 wt % toluene-2,5-diamine sulfate.

Attractive copper shades with very favorable fastness properties have also been produced when 2-(2,5-diaminophenyl)ethanol sulfate is additionally used in certain quantity ranges in the agents according to the present invention as a coupler from the group.

Especially preferred is an agent for oxidatively dyeing keratinous fibers that includes, in a cosmetic carrier, based on the total weight of the agent,
(A) 0.025 to 2.5 wt % 1-(2-hydroxyethyl)-4,5-diamino pyrazole sulfate, and
(B) 0.025 to 1.5 wt % 2,6-dihydroxy-3,4-dimethylpyridine, and
additionally 0.007 to 1.5 wt % 2-(2,5-diaminophenyl)ethanol sulfate.

Especially preferred is an agent for oxidatively dyeing keratinous fibers that includes, in a cosmetic carrier, based on the total weight of the agent,
(A) 0.05 to 1.0 wt % 1-(2-hydroxyethyl)-4,5-diamino pyrazole sulfate, and
(B) 0.05 to 1.0 wt % 2,6-dihydroxy-3,4-dimethylpyridine, and
additionally 0.007 to 0.7 wt % 2-(2,5-diaminophenyl)ethanol sulfate.

Especially preferred is an agent for oxidatively dyeing keratinous fibers that includes, in a cosmetic carrier, based on the total weight of the agent,
(A) 0.1 to 0.7 wt % 1-(2-hydroxyethyl)-4,5-diamino pyrazole sulfate,
(B) 0.1 to 0.5 wt % 2,6-dihydroxy-3,4-dimethylpyridine, and
additionally 0.007 to 0.15 wt % 2-(2, 5-diaminophenyl)ethanol sulfate.

Especially preferred is an agent for oxidatively dyeing keratinous fibers that includes, in a cosmetic carrier, based on the total weight of the agent,
(A) 0.1 to 0.5 wt % 1-(2-hydroxyethyl)-4,5-diamino pyrazole sulfate,
(B) 0.1 to 0.3 wt % 2,6-dihydroxy-3,4-dimethylpyridine, and
additionally 0.07 to 0.1 wt % 2-(2,5-diaminophenyl)ethanol sulfate.

Preferred additional oxidation dye precursors of the developer type may be selected from the group consisting of 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2, 5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 2,4,5,6-tetraaminopyrimidine, 4-hydroxy-2,5,6-triaminopyrimidine, 2-hydroxy-4, 5,6-triaminopyrimidine, 2,3-diamino-6,7-dihydro-1H,5H-pyrazolo[1,2-a]pyrazol-1, and physiologically acceptable salts thereof.

Furthermore, the agents according to the present invention may additionally include one or more oxidation dye precursors of the coupler type, which are distinct from the coupler (B) 2,6-dihydroxy-3,4-dimethylpyridine.

In the context of oxidative dyeing, coupler components alone do not produce any significant dyeing, but instead require the presence of developer components. Coupler components in the sense of the present invention allow at least one substitution of a chemical residue of the coupler by the oxidized form of the developer component. This forms covalent bonds between the coupler and developer components.

Preferably selected as a suitable coupler component according to the present invention is at least one compound from the following classes:
m-aminophenol and/or the derivatives thereof,
m-dihydroxybenzene and/or the derivatives thereof,
m-diaminobenzene and/or the derivatives thereof,
o-diaminobenzene and/or the derivatives thereof,
o-aminophenol derivatives, such as, for example, o-aminophenol,
naphthalene derivatives having at least one hydroxy group,
di- or trihydroxybenzene and/or derivatives thereof,
pyridine derivatives,
pyrimidine derivatives, monohydroxyindole derivatives and/or monoaminoindole derivatives,
monohydroxyindoline derivatives and/or monoaminoindoline derivatives,
pyrazolone derivatives, such as, for example, 1-phenyl-3-methylpyrazol-5-one,
morpholine derivatives, such as, for example, 6-hydroxybenzomorpholine or 6-aminobenzomorpholine,
quinoxaline derivatives, such as, for example, 6-methyl-1,2,3,4-tetrahydroquinoxaline.

Mixtures of two or more compounds from one or more of these classes are also permissible according to the present invention within the framework of this embodiment.

Another preferred embodiment is an agent according to the present invention, characterized by additionally including at least one oxidation dye precursor of the coupler type selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)-amino]-4-methoxy-5-methylphenyl}amino)ethanol, 2-({3-[(2-hydroxyethyl)amino]-2-methoxy-5-methylphenyl}amino)ethanol, 2-(3-[(2-hydroxyethyl)amino]-4, 5-dimethylphenyl}amino)ethanol, 2-([3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2, 4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2, 7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, and/or 7-hydroxyindoline, or mixtures of these compounds or of the physiologically acceptable salts thereof.

In principle, the agents according to the present invention may also include at least one direct dye from the group of the anionic, nonionic, and/or cationic dyes.

This especially preferably entails one or more nonionic direct dyes from the group: HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1, 4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethy)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

In another especially preferred embodiment, an agent according to the present invention is characterized by additionally including one or more nonionic direct dyes from the group HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1, 4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethy)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

It is possible to additionally include anionic direct dyes known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Suitable cationic direct dyes are cationic triphenylmethane dyes such as Basic Blue 7, Basic Blue 26, Basic Violet 2, and Basic Violet 14, aromatic systems that are substituted with a quaternary nitrogen group, for example Basic Yellow 57, Basic Red 76, Basic Blue 99, Basic Brown 16, and Basic Brown 17, anthraquinone dyes such as HC Blue 16 (Bluequat B), and direct dyes having a heterocycle that comprises at least one quaternary nitrogen atom, in particular Basic Yellow 87, Basic Orange 31, and Basic Red 51. The cationic direct dyes that are marketed under the Arianor trademark are likewise suitable cationic direct dyes according to the present invention.

The additional oxidation dye precursors, i.e., developer components and coupler components that are distinct from the compounds of the groups (A) and (B), and the optionally additionally included direct dyes maybe used, for example, in an amount of 0.0001 to 5.0 wt %, preferably 0.001 to 3.5 wt %, in each case based on the total weight of the agent according to the present invention.

The oxidation dye precursors (A) and (B) are formulated in a nonionic base formulation having at least one nonionic surfactant (D) and, to the greatest extent possible, no anionic surfactants (E). Preferably, this nonionic base formulation entails a creamy emulsion. It especially preferably includes one or more additional nonionic components, e.g., $C_{12}$-$C_{30}$ fatty alcohols.

$C_{12}$-$C_{30}$ fatty alcohols may entail saturated, monounsaturated, or polyunsaturated linear or branched fatty alcohols having 12 to 30 C atoms.

Examples of linear saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), gadoleyl alcohol ((9Z)-eicos-9-en-1-ol), arachidonic alcohol ((5Z,8Z,11Z,14Z)-eicosa-5, 8,11,14-tetraen-1-ol), erucyl alcohol ((13Z)-docos-13-en-1-ol), and/or brassidyl alcohol ((13E)-docosen-1-ol).

The preferred representatives for branched fatty alcohols are 2-octyl dodecanol, 2-hexyl dodecanol, and/or 2-butyl dodecanol.

The $C_{12}$-$C_{30}$ fatty alcohol(s) is/are especially preferably included in the agent according to the present invention in a total amount of 1.0 to 10.0 wt %, preferably 1.5 to 7.5 wt %, further preferably 2.0 to 7.0 wt %, and especially preferably 2.5 to 6.5 wt %. All quantities given are again based on the total weight of all $C_{12}$-$C_{30}$ fatty alcohols included in the agent, which is set in relation to the total weight of the agent.

In another particularly preferred embodiment, an agent according to the present invention is characterized by including—based on the total weight of the agent—one or more $C_{12}$-$C_{30}$ fatty alcohols at a total content of 1.0 to 10.0 wt %, preferably 1.5 to 7.5 wt %, further preferably 2.0 to 7.0 wt %, and especially preferably 2.5 to 6.5 wt %.

As additional nonionic components, the nonionic base formulation may additionally include one or more fatty components from the group of $C_{12}$-$C_{30}$ fatty acid triglycerides, $C_{12}$-$C_{30}$ fatty acid diglycerides, and/or $C_{12}$-$C_{30}$ fatty acid monoglycerides.

A $C_{12}$-$C_{30}$ fatty acid triglyceride is understood in the sense of the present invention to be the triester of the trihydric alcohol glycerol with three fatty acid equivalents. Both structurally-identical and distinct fatty acids within a triglyceride molecule may be involved in the ester formations.

Fatty acids are understood, according to the present invention, to be saturated or unsaturated, branched or unbranched, substituted or unsubstituted $C_{12}$-$C_{30}$ carboxyl acids. Unsaturated fatty acids may be monounsaturated or polyunsaturated. With an unsaturated fatty acid, the C—C double bond(s) thereof may have the cis or trans configuration.

Notable for particular suitability are fatty acid triglycerides in which at least one of the ester groups originating from glycerol is formed with a fatty acid, selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], and/or nervonic acid [(15Z)-tetracos-15-enoic acid].

The fatty acid triglycerides may also be of natural origin. The fatty acid triglycerides or mixtures thereof derived from soybean oil, groundnut oil, olive oil, sunflower oil, macadamia nut oil, moringa oil, apricot kernel oil, marula oil and/or optionally hydrogenated castor oil are particularly suitable for use in the products according to the present invention.

A $C_{12}$-$C_{30}$ fatty acid monoglyceride is understood to mean the monoester of the trihydric alcohol, glycerol, with one fatty acid equivalent. Here, either the middle hydroxy group of the glycerol or the terminal hydroxy group of the glycerol may be esterified with the fatty acid.

Notable for particular suitability are $C_{12}$-$C_{30}$ fatty acid monoglycerides in which a hydroxy group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], or nervonic acid [(15Z)-tetracos-15-enoic acid].

A $C_{12}$-$C_{30}$ fatty acid diglyceride is understood to mean the diester of the trihydric alcohol, glycerol, with two fatty acid equivalents. In this case, either the middle and a terminal hydroxy group of glycerol can be esterified with two fatty acid equivalents, or however both terminal hydroxy groups of glycerol are each esterified with one fatty acid. Glycerol can be esterified hereby both with two structurally similar and with two different fatty acids.

Notable for particular suitability are fatty acid diglycerides in which at least one of the ester groups originating from glycerol is formed with a fatty acid, selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,13-trienoic acid], arachidonic acid [(5Z,8Z,11Z,14Z)-eicosa-5,8,11,14-tetraenoic acid], and/or nervonic acid [(15Z)-tetracos-15-enoic acid].

In another particularly preferred embodiment, an agent according to the present invention is characterized by additionally including one or more fatty components from the group of $C_{12}$-$C_{30}$ fatty acid triglycerides, $C_{12}$-$C_{30}$ fatty acid diglycerides, and/or $C_{12}$-$C_{30}$ fatty acid monoglycerides.

The $C_{12}$-$C_{30}$ fatty acid triglycerides, $C_{12}$-$C_{30}$ fatty acid diglycerides, and/or $C_{12}$-$C_{30}$ fatty acid monoglycerides is/are especially preferably included in the ready-to-use agent according to the present invention in a total amount of 0.05 to 2.0 wt %, preferably 0.1 to 1.5 wt %, further preferably 0.1 to 1.0 wt %, and especially preferably 0.2 to 0.9 wt %. All quantities given are again based on the total weight of all $C_{12}$-$C_{30}$ fatty acid monoglycerides, fatty acid diglycerides, and fatty acid triglycerides included in the agent, which is set in relation to the total weight of the agent.

In another particularly preferred embodiment, an agent according to the present invention is characterized by including—based on the total weight of the agent—one or more fatty components from the group of the $C_{12}$-$C_{30}$ fatty acid triglycerides, $C_{12}$-$C_{30}$ fatty acid monoglycerides, and/or $C_{12}$-$C_{30}$ fatty acid diglycerides at a total content of 0.05 to 2.0 wt %, preferably 0.1 to 1.5 wt %, further preferably 0.1 to 1.0 wt %, and especially preferably 0.2 to 0.9 wt %.

The nonionic base formulation may additionally include one or more fatty components from the group of hydrocarbons as further nonionic components.

Hydrocarbons are compounds have eight to 80 C atoms composed exclusively of carbon and hydrogen atoms. Especially preferred in this context are aliphatic hydrocarbons, such as mineral oils, liquid paraffin oils (e.g., paraffinum liquidum or paraffinum perliquidum), isoparaffin oils, semisolid paraffin oils, paraffin waxes, solid paraffin (paraffinum solidum), Vaseline, and polydecene.

In another particularly preferred embodiment, an agent according to the present invention is characterized by additionally including one or more fatty components from the group of hydrocarbons.

The hydrocarbons are especially preferably included in the ready-to-use agent according to the present invention in a total amount of 0.5 to 5.0 wt %, preferably 0.7 to 4.5 wt %, further preferably 1.0 to 4.0 wt %, and especially preferably 1.5 to 3.5 wt %. All quantities given are again based on the total weight of all hydrocarbons included in the agent, which is set in relation to the total weight of the agent.

In another particularly preferred embodiment, an agent according to the present invention is characterized by including—based on the total weight of the agent—one or more fatty components from the group of the hydrocarbons at a total content of 0.5 to 5.0 wt %, preferably 0.7 to 4.5 wt %, further preferably 1.0 to 4.0 wt %, and especially preferably 1.5 to 3.5 wt %.

The agents according to the present invention may moreover include further active agents, auxiliary substances, and additives, including for example nonionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones, such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidinone copolymers quaternized with diethyl sulfate, vinylpyrrolidinone-imidazolinium-methochloride copolymers and quaternized polyvinyl alcohol; zwitterionic and amphoteric polymers; anionic polymers such as polyacrylic acids or crosslinked polyacrylic acids; structuring agents such as glucose, maleic acid and lactic acid, hair-conditioning compounds such as phospholipids, for example lecithin and cephalins; perfume oils, dimethyl isosorbide and cyclodextrins; active agents to improve the fiber structure, in particular mono-, di- and oligosaccharides such as for example glucose, galactose, fructose, fruit sugars and lactose; dyes for coloring the agent; anti-dandruff active agents such as piroctone olamine, zinc omadine, and climbazole; amino acids and oligopeptides; protein hydrolysates of animal and/or plant origin as well as those in the form of the fatty acid condensation products thereof or optionally anionically or cationically modified derivatives thereof; vegetable oils; light stabilizers and UV blockers; active agents such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments as well as propellants such as propane-butane mixtures, $N_2O$, dimethyl ether, CO2, and air.

In a particularly preferred embodiment, the additional active agents, auxiliary substances, and additives that are used in the agent according to the present invention are also nonionic.

The previously described agent according to the present invention involves the ready-to-use agent that already includes both the oxidation dye precursors and the oxidizing agent (hydrogen peroxide). To produce this ready-to-use coloring agent and initiate the dye formation reaction, generally a first dye cream (hereinafter referred to as a component K1) is mixed with a second component K2 including an oxidizing agent.

To avoid incompatibilities and prevent premature, undesired dye formation, the components K1 (dye cream) and K2 (oxidizing agent preparation) are always prepared separately from one another, and are brought into contact with one another only briefly before use. For the consumer, the components (K1) and (K2) are preferably provided in the form of a multicomponent packaging unit (kit-of-parts).

A second subject matter of the present invention is therefore a multicomponent packaging unit (kit-of-parts) for oxidatively dyeing keratinous fibers, comprising at least two components (K1) and (K2) prepared separately from one another, wherein the first component (K1) includes, in a cosmetic carrier,
  (A) 1-(2-hydroxyethyl)-4,5-diamino pyrazole and/or a physiologically acceptable salt thereof,
  (B) 2,6-dihydroxy-3,4-dimethylpyridine, and
  (D') one or more nonionic surfactants,
the second component (K2) includes, in a cosmetic carrier,
  (C) hydrogen peroxide, and
  (D") one or more nonionic surfactants, and
the total content of all of the anionic surfactants (E) included in the component (K1)—based on the total weight of the component (K1)—is below 0.6 wt %, and
the total content of all of the anionic surfactants (E) included in the component (K2)—based on the total weight of the component (K2)—is below 0.6 wt %.

The nonionic surfactant(s) (D') in the component (K1) and the nonionic surfactant(s) (D") in the component (K2) may be the same or different. The especially preferred nonionic surfactants (D')/(D") entail the previously-described especially preferred compounds (D).

Mixing (K1) and (K2) results in a ready-to-use agent, as is detailed in the description of the first subject matter of the present invention.

Regarding the preferred embodiments of the components (A), (B), (C), (D') and (D"), and (E), what was stated for the agent according to the present invention applies mutatis mutandis as well.

In an especially preferred embodiment, the multicomponent packaging unit (kit-of-parts) according to the present invention is characterized in that the total content of all of the anionic surfactants (E) included in the component (K1)—based on the total weight of the component (K1)—is below 0.1 wt %, and
the total content of all of the anionic surfactants (E) included in the component (K2)—based on the total weight of the component (K2)—is below 0.1 wt %.

The first component involves the dye preparation (K1) (preferably adjusted so as to be alkaline) including the oxidation dye precursors (A) and (B) (and optionally still more additional oxidation dye precursors and/or more direct dyes).

Prior to use, this dye preparation is mixed with an oxidizing agent preparation (K2). For stability reasons, the oxidizing agent preparation (K2) is preferably adjusted to an acidic pH value and includes the oxidizing agent. The oxidizing agent is hydrogen peroxide, which is usually used in the form of an aqueous solution thereof.

The components (K1) and (K2) may be mixed together at different weight ratios (K1)/(K2), e.g., 0.3 to 3.0, preferably 0.5 to 2.5, and especially preferably 0.45 to 1.5.

An especially preferred method is therefore characterized in that the first component (K1) and the second component (K2) are mixed with one another at a weight ratio (K1)/(K2) of 0.3 to 3.0, preferably 0.45 to 2.5, and especially preferably 0.5 to 1.5.

In addition, the multicomponent packaging unit according to the present invention may also include yet another one or more separately-prepared components. This or these additional separately-prepared component(s) may entail, for example, a pre-treatment agent and/or a post-treatment agent.

For the keratin fibers to be sufficiently swelled, the ready-to-use oxidative coloring agent is preferably adjusted to an alkaline pH value. Also, the dyeing processes performed on the keratin fibers are usually run in an alkaline environment. To protect the keratin fibers as well as the skin as much as possible, however, it is not desirable to adjust to too high a pH value. It is therefore preferable if the pH value of the ready-to-use agent is at a value of 8.0 to 10.5, further preferably 8.7 to 10.3, still further preferably 9.0 to 10.2, and especially preferably 9.2 to 10.1 The pH values given refer to values that have been measured at a temperature of 22° C. with a glass electrode.

The alkalizing agents required to adjust the alkaline pH are generally prepared together with the oxidation dye precursors in the component K1. The alkalizing agents that can be used according to the present invention may be selected from the group consisting of ammonia, alkanolamines, basic amino acids, and inorganic alkalizing agents such as alkali/alkaline-earth metal hydroxides, alkali/alkaline-earth metal silicates, alkali/alkaline-earth metal phosphates, and alkali/alkaline-earth metal hydrogen phosphates. Preferred inorganic alkalizing agents are sodium hydroxide, potassium hydroxide, sodium silicate, and sodium metasilicate. Organic alkalizing agents that can be used according to the present invention are preferably selected from monoethanolamine, 2-amino-2-methylpropanol, and triethanolamine. The basic amino acids that can be used as an alkalizing agent according to the present invention are preferably selected from the group consisting of arginine, lysine, ornithine, and histidine, especially preferably arginine. However, in the framework of the investigations conducted for the present invention, it has been found that agents that are preferred according to the present invention are furthermore characterized by additionally including an organic alkalizing agent. One embodiment of the first subject matter of the present invention is characterized in that the agent additionally includes at least one alkalizing agent selected from the group consisting of ammonia, alkanolamines, and basic amino acids, especially ammonia, monoethanolamine, and arginine or acceptable salts thereof. The alkalizing agent(s) is/are preferably prepared together with the oxidation dye precursors in the dye preparation (K1).

The second component (K2) entails an oxidizing agent preparation including hydrogen peroxide. In a preferred embodiment, hydrogen peroxide itself is used as an aqueous solution in the oxidizing agent preparation (K2). The concentration of a hydrogen peroxide solution in the dye preparation (K2) is determined by the legal requirements on one hand and by the desired effect on the other hand; preferably, 6% to 12% solutions in water are used. Preparations (K2) that are preferred according to the present invention characterized by including 5 to 20 wt %, preferably 1 to 12.5 wt %, especially preferably 2.5 to 10 wt %, and, in particular, 3 to 6 wt % hydrogen peroxide, based in each case on the total weight of the oxidizing agent preparation (K2).

What has been stated regarding the agents according to the present invention also applies, mutatis mutandis, to additional preferred embodiments of the multicomponent packaging unit (kit-of-parts) according to the present invention.

EXAMPLES 1.1. Production of the Coloring Agent

The following dye creams were produced (all quantities refer to percent by weight, unless other indicated):

| Dye creams | F(V1) | F(E1) | F(V2) | F(E2) | F(V3) | F(E3) |
|---|---|---|---|---|---|---|
| Cetyl alcohol (C16 fatty alcohol) | 3.6 | 3.6 | 3.6 | 3.6 | 3.6 | 3.6 |
| Stearyl alcohol (C18 fatty alcohol) | 2.0 | 2.0 | 2.0 | 2.0 | 2.0 | 2.0 |
| Paraffinum Liquidum | 2.1 | 2.1 | 2.1 | 2.1 | 2.1 | 2.1 |
| Glycerol monostearate | — | 0.6 | — | 0.6 | — | 0.6 |
| Ceteareth-30, $C_{16}$-$C_{18}$ fatty alcohols, ethoxylated (30 EO) | 1.2 | 1.2 | 1.2 | 1.2 | 1.2 | 1.2 |
| Ceteareth-100, $C_{16}$-$C_{18}$ fatty alcohols, ethoxylated (100 EO) | — | 0.6 | — | 0.6 | — | 0.6 |
| Sodium laureth-6 carboxylate | 2.1 | — | 2.1 | — | 2.1 | — |
| Sodium myreth sulfate Sodium myristyl ether sulfate (3 EO) | 1.96 | — | 1.96 | — | 1.96 | — |
| 1-(2-Hydroxyethyl)-4,5-diamino pyrazole sulfate | 0.70 | 0.70 | 0.70 | 0.70 | 0.70 | 0.70 |
| 2,6-dihydroxy-3,4-dimethylpyridine | 0.45 | 0.45 | 0.43 | 0.43 | 0.38 | 0.38 |
| p-Toluylenediamine sulfate | 0.132 | 0.132 | 0.132 | 0.132 | 0.132 | 0.132 |
| Resorcinol | — | — | 0.022 | 0.022 | — | — |
| 2-amino-3-hydroxy-pyridine | — | — | — | — | 0.066 | 0.066 |
| 1,2-Propanediol | 6.0 | 6.0 | 6.0 | 6.0 | 6.0 | 6.0 |
| Ammonia (25% aqueous solution) | 7.0 | 7.0 | 7.0 | 7.0 | 7.0 | 7.0 |

-continued

| Dye creams | F(V1) | F(E1) | F(V2) | F(E2) | F(V3) | F(E3) |
|---|---|---|---|---|---|---|
| Sodium sulfite | 0.3 | 0.3 | 0.3 | 0.3 | 0.3 | 0.3 |
| Vitamin C (ascorbic acid) | 0.1 | 0.1 | 0.1 | 0.1 | 0.1 | 0.1 |
| Ammonium sulfate | 0.65 | 0.65 | 0.65 | 0.65 | 0.65 | 0.65 |
| Water | up to 100 | up to 100 | up to 100 | up to 100 | up to 100 | up to 100 |

The dye cream F(V) was mixed in each case at a weight ratio of 1:1 with the oxidizing agent preparation Ox(V) (comparison).

The dye cream F(E) was mixed in each case at a weight ratio of 1:1 with the oxidizing agent preparation Ox(E) (invention).

| Dye creams | Ox (V) | Ox (E) |
|---|---|---|
| Dipicolinic acid | 0.1 | 0.1 |
| Sodium hydroxide (50% aqueous solution) | 0.76 | 0.76 |
| Disodium pyrophosphate | 0.03 | 0.03 |
| Etidronic acid (1-hydroxyethane 1,1-diphosphonic acid, 60% aqueous solution) | 1.5 | 1.5 |
| Sodium laureth sulfate (sodium lauryl ether sulfate) (EO 2) | 0.65 | — |
| Acrylate copolymer (27.5% to 28.5%) | 4.3 | — |
| 1,2-Propanediol | — | 0.5 |
| Paraffinum Liquidum | — | 2.0 |
| Cetearyl alcohol ($C_{16}/C_{18}$ fatty alcohols) | — | 3.6 |
| Ceteareth-20 | — | 1.2 |
| Hydrogen peroxide (50% aqueous solution) | 12.0 | 12.0 |
| Water | up to 100 | up to 100 |

1.2. Application

The previously-produced and ready-to-use oxidative coloring agents (F(V)+Ox(V) and F(E)+Ox(E)) were each applied to the strands of hair (buffalo stomach hair) and allowed to interact for a period of 30 minutes at room temperature. The strands were then rinsed for one minute with lukewarm tap water and dried in a cold air flow. Next, each strand of hair was measured colorimetrically. Five measurement values were obtained per formulation, and the mean value was taken in each case from these measurement values.

1.3. Determining the Chroma

In colorimetry (i.e., in the Lab color space), the L-value describes the brightness of a color with values from 0 to 100.

In the Lab color space, the L-axis at the zero point is perpendicular to the plane formed by the a- and b-axes. The L-axis can also be called the neutral gray axis, because (with a=0 and b=0) all of the achromatic colors (gray tones) are included between the endpoints black (L=0) and white (L=100).

The color richness of a color can be quantitatively described by determining the value of the chroma.

The chroma value (C) of the dyed strands of hair is obtained according to the following formula $$C=\sqrt{a^2+b^2}$$

The chroma value is thus directly proportional to the color richness of a dye. The higher the chroma value, the higher the color richness of the dye.

When the dyed strands of hair were colorimetrically measured, the following values were obtained:

| Application mix | L | a | b | C |
|---|---|---|---|---|
| F(V1) + Ox(V) (comparison) | 42.96 | 20.24 | 23.36 | 30.90 |
| F(E1) + Ox(E) (according to the present invention) | 43.34 | 27.13 | 35.39 | 44.59 |
| F(V2) + Ox(V) (comparison) | 37.61 | 26.69 | 24.85 | 36.46 |
| F(E2) + Ox(E) (according to the present invention) | 40.92 | 27.42 | 32.25 | 42.33 |
| F(V3) + Ox(V) (comparison) | 30.92 | 20.79 | 16.92 | 26.81 |
| F(E3) + Ox(E) (according to the present invention) | 33.86 | 26.78 | 25.74 | 37.14 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for oxidatively dyeing keratinous fibers, in particular human hair, comprising, in a cosmetic carrier:
   (A) 1-(2-hydroxyethyl)-4,5-diamino pyrazole and/or a physiologically acceptable salt thereof,
   (B) 2,6-dihydroxy-3,4-dimethylpyridine,
   (C) hydrogen peroxide, and
   (D) one or more nonionic surfactants,
wherein a total content of any anionic surfactants (E) included in the agent is below 0.6 wt %, based on the total weight of the agent.

2. The agent according to claim 1, comprising:
   (A) 0.025 to 2.5 wt % 1-(2-hydroxyethyl)-4,5-diamino pyrazole sulfate, based on the total weight of the agent.

3. The agent according to claim 1, comprising:
   (B) 0.025 to 1.5 wt %, 2,6-dihydroxy-3,4-dimethylpyridine, based on the total weight of the agent.

4. The agent according to claim 1, wherein the one or more nonionic surfactants (D) comprise (D1) one or more ethoxylated fatty alcohols of formula (I), $$R_1\text{—}[O\text{—}CH_2\text{—}CH_2]_n\text{—}OH \quad (I)$$

wherein
   R1 denotes a saturated or unsaturated unbranched or branched $C_8$-$C_{30}$ alkyl group, and
   n denotes an integer from 10 to 120.

5. The agent according to claim 1, wherein the one or more nonionic surfactants (D) comprise (D2) one or more alkyl mono- or polyglucosides of formula (II), (II)

wherein
   m denotes an integer 7 to 21, and
   denotes an integer 1 to 4.

6. The agent according to claim 1, wherein a total content of all nonionic surfactants (D) included in the agent — based on the total weight of the agent — is 0.3 to 5.0 wt %.

7. The agent according to claim 1, wherein a total content of all anionic surfactants (E) included in the agent — based on the total weight of the agent — is below 0.1 wt %.

8. The agent according to claim 1, wherein a total content of any anionic surfactants selected from the group consisting of
- (E1) sodium, potassium, and ammonium salts of fatty acids,
- (E2) sodium, potassium, and ammonium salts of alkyl sulfates,
- (E3) sodium, potassium, and ammonium salts of alkyl ether sulfates, and
- (E4) sodium, potassium, and ammonium salts of ether carboxylic acids, are at a concentration — based on the total weight of the agent — below 0.1 wt %.

9. The agent according to claim 1, wherein any zwitterionic surfactants (F) included in the agent — based on the total weight of the agent — is below a concentration of 0.5 wt %.

10. The agent according to claim 1, further comprising one or more compounds selected from the group consisting of p-phenylenediamine, toluene-2,5-diamine, 2-(2,5-diaminophenyl)ethanol, and the physiologically acceptable salts of these compounds.

11. The agent according to claim 1, further comprising one or more $C_{12}$-$C_{30}$ fatty alcohols at a total content of 1.0 to 10.0 wt %, based on the total weight of the agent.

12. The agent according to claim 1, further comprising one or more fatty components selected from the group consisting of $C_{12}$-$C_{30}$ fatty acid triglycerides, $C_{12}$-$C_{30}$ fatty acid monoglycerides, and $C_{12}$-$C_{30}$ fatty acid diglycerides at a total content of 0.05 to 2.0 wt %, based on the total weight of the agent.

13. An agent according to claim 1, further comprising one or more fatty components selected from the group consisting of hydrocarbons at a total content of 0.5 to 5.0 wt %, based on the total weight of the agent.

14. A multicomponent packaging unit (kit-of-parts) for oxidatively dyeing keratinous fibers, comprising components (K1) and (K2) prepared separately from one another, wherein
the first component (K1) comprises, in a cosmetic carrier:
- (A) 1-(2-hydroxyethyl)-4,5-diamino pyrazole and/or a physiologically acceptable salt thereof,
- (B) 2,6-dihydroxy-3,4-dimethylpyridine, and (D') one or more nonionic surfactants, the second component (K2) comprises, in a cosmetic carrier:
- (C) hydrogen peroxide, and
- (D") one or more nonionic surfactants, the total content of all of the anionic surfactants (E) in the component (K1) is below 0.6 wt %, based on the total weight of the component (K1), and
the total content of all of the anionic surfactants (E) in the component (K2) is below 0.6 wt %, based on the total weight of the component (K2).

15. The multicomponent packaging unit (kit-of-parts) according to claim 14, wherein:
the total content of all of the anionic surfactants (E) in the component (K1) below 0.1 wt %, based on the total weight of component (K1) and
the total content of all of the anionic surfactants (E) in the component (K2) is below 0.1 wt %, based on the total weight of component (K1).

16. The agent according to claim 1, wherein the agent does not contain any added anionic surfactants (E).

17. The multicomponent packaging unit (kit-of-parts) according to claim 14, wherein the component (K1) and the component (K2) are both formulated without an anionic surfactant (E).

18. An agent for oxidatively dyeing keratinous fibers, comprising:
a cosmetic carrier,
- (A) 1-(2-hydroxyethyl)-4,5-diamino pyrazole and/or a physiologically acceptable salt thereof,
- (B) 2,6-dihydroxy-3,4-dimethylpyridine,
- (C) hydrogen peroxide, and
- (D) one or more nonionic surfactants, wherein the agent does not contain any added anionic surfactants (E).

19. The agent of claim 18, further comprising based on the total weight of the agent, 1.0 to 10.0 wt. % of one or more $C_{12}$-$C_{30}$ fatty alcohols.

20. The agent of claim 19, wherein the nonionic surfactants (D) are selected from the group consisting of: alkyl polyglycols, alkene polyglycols, alkyl saccharides, alkene polysaccharides, and mixtures thereof.

* * * * *